US012137970B2

United States Patent
Favreau et al.

(10) Patent No.: US 12,137,970 B2
(45) Date of Patent: *Nov. 12, 2024

(54) DEVICES AND METHODS FOR INDUCING ABLATION IN OR AROUND OCCLUDED IMPLANTS

(71) Applicant: Boston Scientific Scimed, Inc., Maple Grove, MN (US)

(72) Inventors: John T. Favreau, Spencer, MA (US); Travis Henchie, Worcester, MA (US); Karim Tarabein, Shaker Heights, OH (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/481,996

(22) Filed: Oct. 5, 2023

(65) Prior Publication Data
US 2024/0024025 A1    Jan. 25, 2024

Related U.S. Application Data

(63) Continuation of application No. 16/717,439, filed on Dec. 17, 2019, now Pat. No. 11,813,018.
(Continued)

(51) Int. Cl.
*A61B 18/14* (2006.01)
*A61B 17/00* (2006.01)
(Continued)

(52) U.S. Cl.
CPC .............. *A61B 18/1492* (2013.01); *A61B 2017/00336* (2013.01); *A61B 2017/00867* (2013.01);
(Continued)

(58) Field of Classification Search
CPC ...... A61B 18/1492; A61B 2017/00336; A61B 2018/00577; A61B 2018/126; A61B 2018/144
See application file for complete search history.

(56) References Cited

U.S. PATENT DOCUMENTS

| 4,392,040 A | 7/1983 | Rand et al. |
| 5,078,736 A | 1/1992 | Behl |

(Continued)

FOREIGN PATENT DOCUMENTS

| WO | 2005030071 A1 | 4/2005 |
| WO | 2006095171 A1 | 9/2006 |

(Continued)

OTHER PUBLICATIONS

International Search Report and Written Opinion dated Apr. 3, 2020 for International Application No. PCT/US2019/066882.

*Primary Examiner* — Joseph A Stoklosa
*Assistant Examiner* — Annie L Shoulders
(74) *Attorney, Agent, or Firm* — Seager, Tufte & Wickhem, LLP

(57) ABSTRACT

A bipolar ablation device for treatment of a stenosis within an implanted metallic stent may include an elongate shaft slidably disposable within an endoscope, the elongate shaft including at least one electrode configured to form a first pole of the bipolar ablation device, and an electrode lead slidably disposable within the endoscope. The electrode lead may be configured to electrically engage the implanted metallic stent to form a second pole of the bipolar ablation device. The elongate shaft may be positionable within a lumen of the implanted metallic stent.

20 Claims, 21 Drawing Sheets

Related U.S. Application Data

(60) Provisional application No. 62/781,305, filed on Dec. 18, 2018.

(51) Int. Cl.
    *A61B 18/00*     (2006.01)
    *A61B 18/12*     (2006.01)
    *A61B 90/00*     (2016.01)

(52) U.S. Cl.
    CPC ............... *A61B 2018/00404* (2013.01); *A61B 2018/00488* (2013.01); *A61B 2018/00535* (2013.01); *A61B 2018/00577* (2013.01); *A61B 2018/00613* (2013.01); *A61B 2018/126* (2013.01); *A61B 2018/144* (2013.01); *A61B 2090/3966* (2016.02)

(56) References Cited

U.S. PATENT DOCUMENTS

| | | | |
|---|---|---|---|
| 5,749,914 | A | 5/1998 | Janssen |
| 5,941,869 | A | 8/1999 | Patterson et al. |
| 5,980,563 | A | 11/1999 | Tu et al. |
| 6,102,908 | A | 8/2000 | Tu et al. |
| 6,129,725 | A | 10/2000 | Tu et al. |
| 6,228,109 | B1 | 5/2001 | Tu et al. |
| 6,319,251 | B1 | 11/2001 | Tu et al. |
| 6,648,881 | B2 | 11/2003 | KenKnight et al. |
| 8,313,482 | B2 | 11/2012 | McIntyre et al. |
| 8,357,153 | B2 | 1/2013 | Habib |
| 8,753,342 | B2 | 6/2014 | Habib et al. |
| 9,011,430 | B2 | 4/2015 | Habib |
| 9,713,730 | B2 | 7/2017 | Mathur et al. |
| 11,160,571 | B2 | 11/2021 | Nguyen et al. |
| 2002/0072743 | A1 | 6/2002 | KenKnight et al. |
| 2004/0215310 | A1 | 10/2004 | Amirana |
| 2005/0171534 | A1 | 8/2005 | Habib |
| 2009/0143777 | A1 | 6/2009 | Pacey et al. |
| 2009/0222000 | A1 | 9/2009 | Pacey |
| 2009/0228001 | A1 | 9/2009 | Pacey |
| 2010/0049191 | A1 | 2/2010 | Habib et al. |
| 2010/0268217 | A1 | 10/2010 | Habib |
| 2010/0331949 | A1 | 12/2010 | Habib |
| 2011/0004206 | A1 | 1/2011 | Habib et al. |
| 2011/0208181 | A1 | 8/2011 | Habib |
| 2012/0109282 | A1 | 5/2012 | Johnson et al. |
| 2013/0211176 | A1 | 8/2013 | Habib |
| 2013/0218155 | A1 | 8/2013 | Habib et al. |
| 2015/0134044 | A1 | 5/2015 | Kim et al. |
| 2016/0022353 | A1* | 1/2016 | Forsyth .................. A61B 34/10 606/34 |
| 2017/0224415 | A1 | 8/2017 | Dong et al. |
| 2017/0231684 | A1 | 8/2017 | Johnson et al. |
| 2017/0281193 | A1 | 10/2017 | Asirvatham et al. |
| 2018/0168721 | A1 | 6/2018 | Sperling |
| 2018/0303595 | A1 | 10/2018 | Opie et al. |
| 2019/0021781 | A1 | 1/2019 | Drasler et al. |
| 2019/0290300 | A1 | 9/2019 | Shuman et al. |
| 2020/0129316 | A1 | 4/2020 | Kawwas et al. |
| 2021/0393948 | A1 | 12/2021 | Opie et al. |

FOREIGN PATENT DOCUMENTS

| | | |
|---|---|---|
| WO | 2007101986 A1 | 9/2007 |
| WO | 2007135431 A2 | 11/2007 |
| WO | 2007135437 A1 | 11/2007 |
| WO | 2008009972 A2 | 1/2008 |
| WO | 2008084244 A2 | 7/2008 |
| WO | 2008084252 A2 | 7/2008 |
| WO | 2008009972 A3 | 8/2008 |
| WO | 2008084244 A3 | 10/2008 |
| WO | 2011055143 A2 | 5/2011 |
| WO | 2011055143 A3 | 10/2011 |
| WO | 2011161474 A1 | 12/2011 |

\* cited by examiner

DEVICES AND METHODS FOR INDUCING ABLATION IN OR AROUND OCCLUDED IMPLANTS

CROSS-REFERENCE TO RELATED APPLICATIONS

This application is a continuation of U.S. patent application Ser. No. 16/717,439, filed Dec. 17, 2019, which claims the benefit of U.S. Provisional Application No. 62/781,305 filed Dec. 18, 2018, the entire disclosures of which are hereby incorporated by reference.

TECHNICAL FIELD

The disclosure relates generally to medical devices, systems, and/or methods for inducing ablation in and/or around an implant, such as a stent or endoprosthesis.

BACKGROUND

A stent may be configured to be positioned in a body lumen for a variety of medical applications. For example, a stent may be used to treat a stenosis in a blood vessel and/or used to maintain patency of a fluid opening or pathway across a stricture of a body lumen, such as in the vascular, urinary, biliary, tracheobronchial, esophageal, gastrointestinal, or renal tracts. In some instances, a bare metal stent may be the medical device and/or implant selected for a particular application. In some cases, tissue ingrowth into openings of the bare metal stent may occur over time, leading to restenosis and/or occlusion of the stent lumen. Several means and/or methods of treating restenosis of the vasculature are available, including atherectomy, angioplasty, etc. In the gastrointestinal and pancreaticobiliary ducts, restenosis of stents can be treated with placement of additional stents, balloon dilation or with RF ablation. Of the known medical devices and methods, each has certain advantages and disadvantages. There is an ongoing need to provide alternative medical devices as well as alternative methods for manufacturing and using medical devices.

SUMMARY

In a first aspect, a bipolar ablation device for treatment of a stenosis within an implanted metallic stent may comprise an elongate shaft slidably disposable within an endoscope, the elongate shaft including at least one electrode configured to form a first pole of the bipolar ablation device; and an electrode lead slidably disposable within the endoscope, the electrode lead being configured to electrically engage the implanted metallic stent to form a second pole of the bipolar ablation device. The elongate shaft may be positionable within a lumen of the implanted metallic stent.

In addition or alternatively, the electrode lead includes an engagement feature configured to releasably contact the electrode lead to the implanted metallic stent.

In addition or alternatively, the engagement feature includes a grasping metallic clip.

In addition or alternatively, the engagement feature includes at least one flared metallic element.

In addition or alternatively, the engagement feature includes an expandable metallic cage.

In addition or alternatively, the engagement feature includes a magnetic coupler.

In addition or alternatively, the engagement feature includes at least one electrode element disposed on an outer surface of an inflatable balloon.

In addition or alternatively, the bipolar ablation device may further comprise an energy source in electrical communication with the at least one electrode and the electrode lead.

In addition or alternatively, the at least one electrode, when positioned within the implanted metallic stent, is configured for directional ablation of the stenosis.

In addition or alternatively, the electrode lead is independently moveable relative to the elongate shaft.

In addition or alternatively, a system for maintaining patency of a body lumen may comprise a metallic stent configured for implantation within the body lumen; and an elongate shaft slidably disposable within an endoscope and configured to extend into a lumen of the metallic stent, the elongate shaft including at least one electrode configured to form a first pole of a bipolar ablation device. The metallic stent may include an electrode lead electrically engageable with a probe extendable through the endoscope such that the metallic stent forms a second pole of the bipolar ablation device.

In addition or alternatively, energization of the bipolar ablation device directs ablation energy within the lumen of the metallic stent.

In addition or alternatively, a metallic stent for maintaining patency of a body lumen may comprise a first electrode wire configured to form a first pole of a bipolar ablation device; a second electrode wire spaced apart from the first electrode wire, the second electrode wire being configured to form a second pole of the bipolar ablation device; and at least one non-conductive filament interwoven with the first electrode wire and the second electrode wire.

In addition or alternatively, the first electrode wire extends helically around a central longitudinal axis of the metallic stent in a first direction, and the second electrode wire extends helically around the central longitudinal axis of the metallic stent in the first direction parallel to the first electrode wire.

In addition or alternatively, the at least one non-conductive filament extends helically around the central longitudinal axis of the metallic stent in a second direction opposite the first direction.

In addition or alternatively, the first electrode wire and the second electrode wire are electrically connectable to an energy source configured to supply bipolar ablation energy.

In addition or alternatively, a method of treating a stenosis within an implanted metallic stent may comprise: advancing an elongate shaft into a lumen of the implanted metallic stent, the elongate shaft including at least one electrode configured to form a first pole of a bipolar ablation device; advancing an electrode lead into electrical contact with the implanted metallic stent such that the implanted metallic stent forms a second pole of the bipolar ablation device; and energizing the bipolar ablation device with the at least one electrode disposed within the lumen of the implanted metallic stent.

In addition or alternatively, energizing the bipolar ablation device directs ablation energy within the lumen of the implanted metallic stent.

In addition or alternatively, at least one of the elongate shaft or the electrode lead is advanceable to the implanted metallic stent within an endoscope.

In addition or alternatively, the method may further comprise connecting the at least one electrode and the electrode lead to an energy source.

In addition or alternatively, energizing the bipolar ablation device provides omnidirectional ablation energy between the at least one electrode and the implanted metallic stent.

In addition or alternatively, the stenosis includes non-concentric tissue ingrowth and the at least one electrode is configured to direct ablation energy toward the non-concentric tissue ingrowth.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
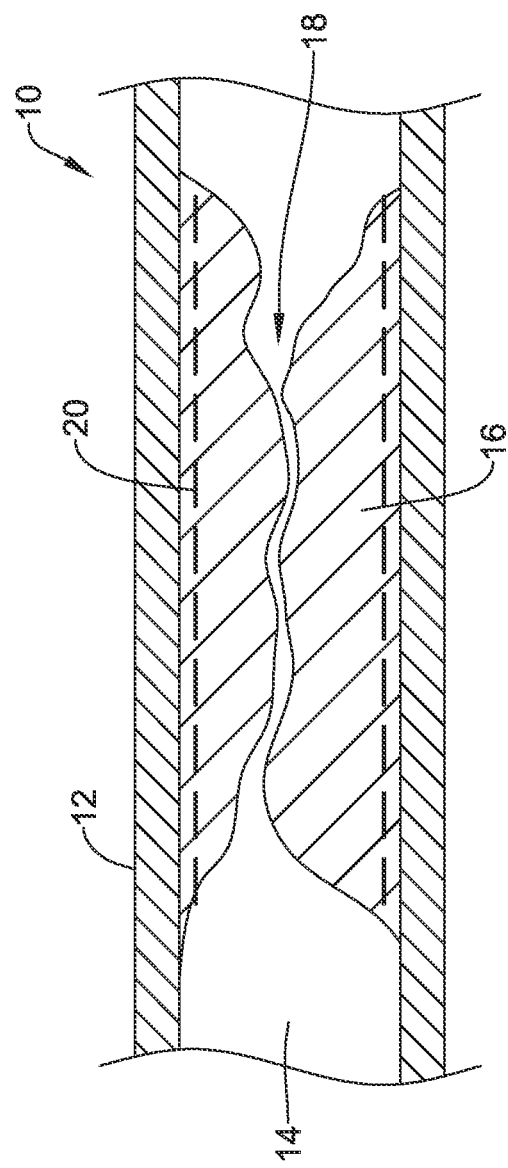
FIG. 1 is a schematic partial cross-sectional view of a previously-implanted stent disposed in a partially-occluded body lumen.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention. However, in the interest of clarity and ease of understanding, while every feature and/or element may not be shown in each drawing, the feature(s) and/or element(s) may be understood to be present regardless, unless otherwise specified. As such, in any given figure, some features may not be shown, or may be shown schematically, for simplicity. Additional details regarding some components, configurations, and/or embodiments may be illustrated in other figures in greater detail.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal"

and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean an outer dimension, "radial extent" may be understood to mean a radial dimension, "longitudinal extent" may be understood to mean a longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete structures or elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

FIG. 1 illustrates, in cross-section, a body lumen 10 having a body lumen wall 12 defining a lumen 14. In some instance, the body lumen 10 may be a blood vessel, trachea, esophagus, colon, pancreatic duct, biliary duct, or other body lumen. The body lumen 10 includes a previously-implanted metallic stent 20 disposed within the lumen 14 and/or in apposition with the body lumen wall 12. The body lumen 10 illustrated in FIG. 1 has undergone tissue ingrowth to form an at least partial occlusion 16 (e.g., stenosis, etc.) of the lumen 14. In some embodiments, the at least partial occlusion 16 may be irregular and/or eccentric within the lumen 14 and/or the metallic stent 20. In some embodiments, the at least partial occlusion 16 may define an occlusion lumen 18 through the at least partial occlusion 16 that is nonconcentric and/or non-coaxial with the lumen 14 of the body lumen 10 and/or the metallic stent 20, off-center with respect to the lumen 14 of the body lumen 10 and/or the metallic stent 20, and/or eccentric with respect to the lumen 14 of the body lumen 10 and/or the metallic stent 20. The metallic stent 20 may include an expandable framework defining a plurality of cells, a plurality of struts, and/or a plurality of rows. The metallic stent 20 may be formed as any one of a variety of known metallic stent configurations, including but not limited to, a cut stent formed from a mololithic tube, a braided stent formed of a plurality of interwoven filaments or wires, a knitted stent formed of one or more filaments or wires, etc. The metallic stent 20 may be configured to shift between a reduced diameter delivery configuration and an expanded deployed or implanted configuration. In some embodiments, the metallic stent 20 may be self-expanding, partially self-expanding, mechanically and/or balloon expandable, and/or combinations thereof. Some suitable, but non-limiting, examples of materials for the metallic stent 20 are discussed below.

Figure 2:
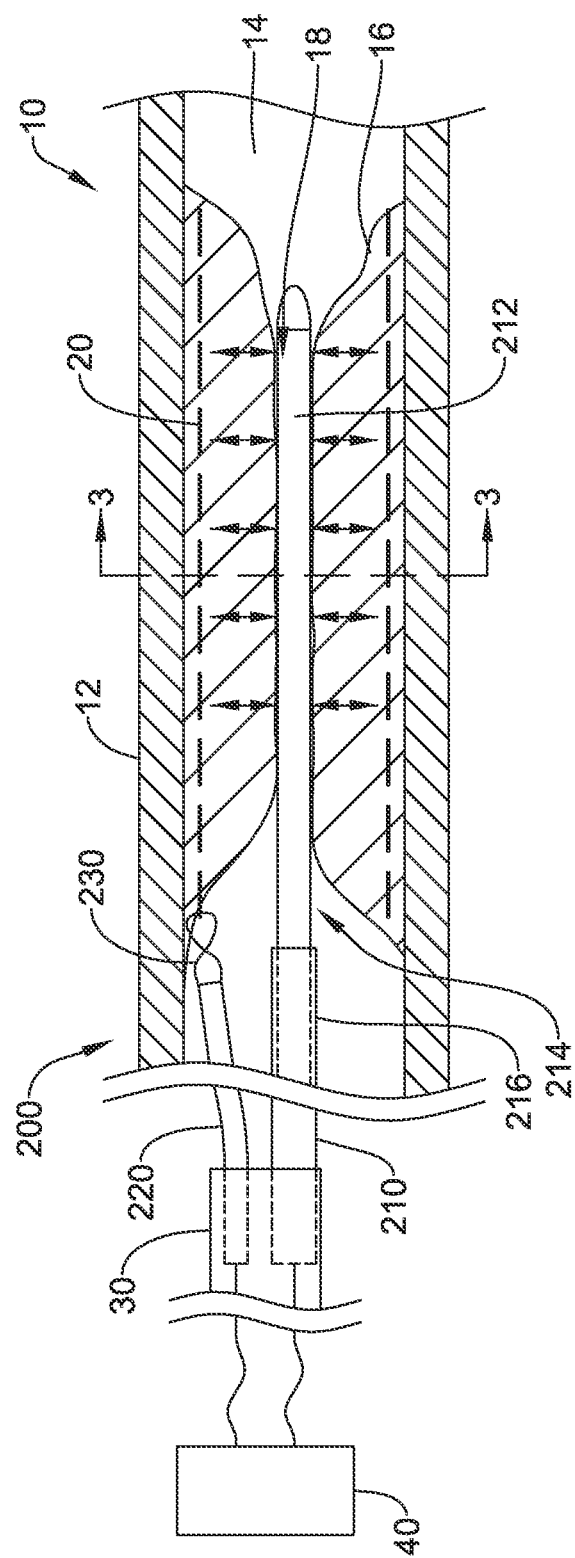
FIG. 2 is a schematic partial cross-sectional view illustrating aspects of an example bipolar ablation device.

FIG. 2 illustrates a bipolar ablation device 200 for treatment of a stenosis and/or the at least partial occlusion 16 within the implanted metallic stent 20 using radiofrequency (RF), irreversible electroporation (IRE), or thermal ablation. In some embodiments, the bipolar ablation device 200 may include an elongate shaft 210 slidably disposable within an endoscope 30, the elongate shaft 210 including at least one electrode 212 configured to form a first pole of the bipolar ablation device 200, and an electrode lead 220 slidably disposable within the endoscope 30, the electrode lead 220 being configured to electrically engage the implanted metallic stent 20 to form a second pole of the bipolar ablation device 200, the first and second poles being a opposite polarities. The electrode lead 220 may be independently movable relative to the elongate shaft 210. In at least some embodiments, the electrode lead 220 may include an engagement feature 230 configured to releasably contact and/or connect the electrode lead 220 to the implanted metallic stent 20. In some embodiments, the elongate shaft 210 may be positionable within a lumen of the implanted metallic stent 20 and/or within the occlusion lumen 18. In some embodiments, the bipolar ablation device 200 may include an energy source 40 configured to be in electrical communication with the at least one electrode 212 and the electrode lead 220. The energy source 40 may be capable of supplying bipolar energy to the first pole (e.g., the implanted metallic stent 20) and the second pole (e.g., the at least one electrode 212) of the bipolar ablation device 200. In some examples, the energy source 40 may be an RF generator.

Figure 3A:
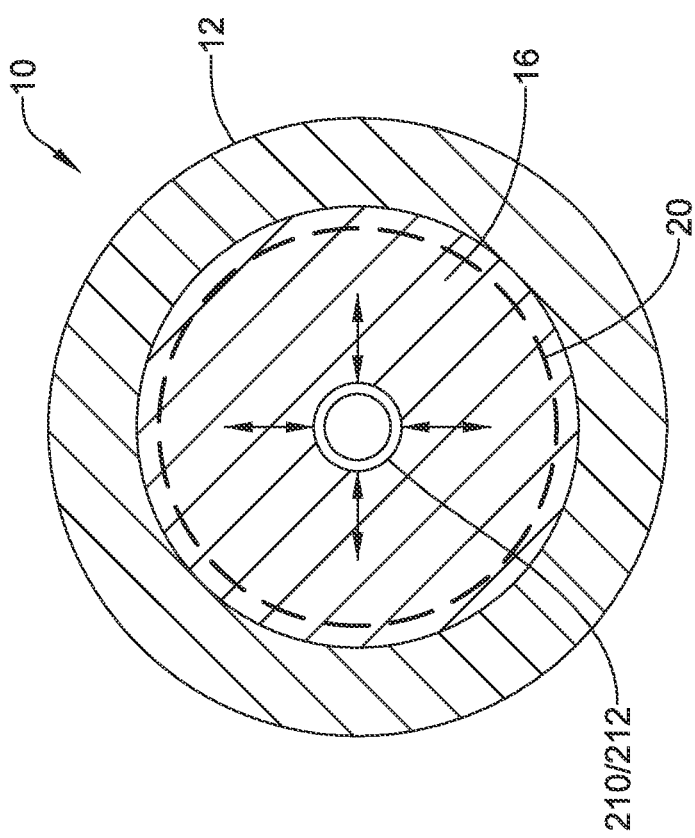
FIGS. 3A and 3B are alternative cross-sectional views taken along the line 3-3 in FIG. 2.
Figure 3B:
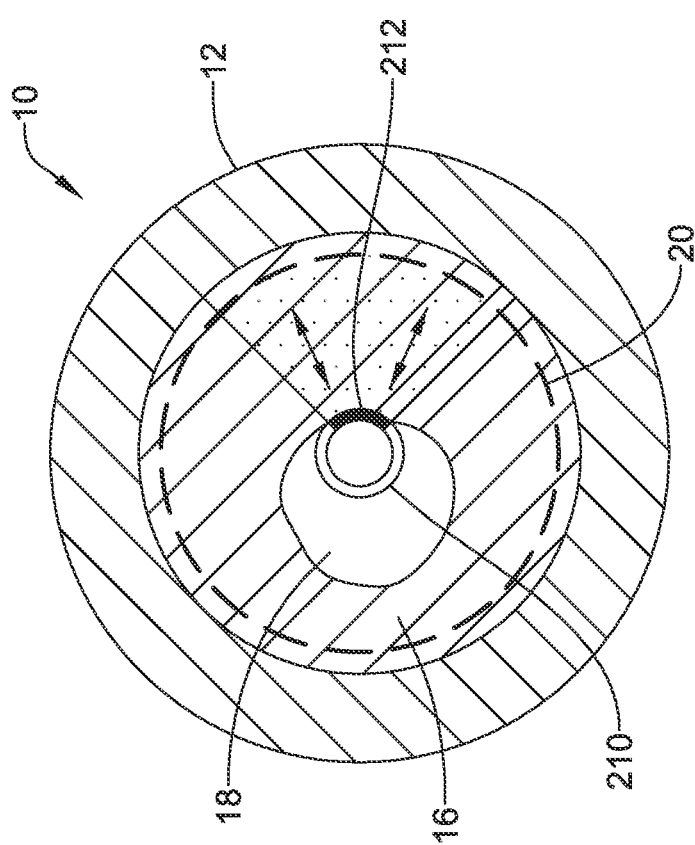

In some embodiments, the at least one electrode 212 may be formed from the elongate shaft 210 itself. For example, the elongate shaft 210 may be metallic and have a bare portion and/or an exposed distal portion 214 forming the at least one electrode 212. In some embodiments, the elongate shaft 210 may include an insulator 216 diposed over and/or on at least a portion of the elongate shaft 210 proximal of the at least one electrode 212. In some embodiments, the at least one electrode 212, when positioned within the implanted metallic stent 20, may be configured to provide omnidirectional ablation energy between the at least one electrode 212 and the implanted metallic stent 20. In some embodiments, the at least one electrode 212, when positioned within the implanted metallic stent 20, may be configured to provide omnidirectional ablation of the stenosis and/or the at least partial occlusion 16, as seen in FIG. 3A. In some embodiments, the at least one electrode 212 may include one electrode, two electrodes, three electrodes, four electrodes, five electrodes, six electrodes, seven electrodes, eight electrodes, or more electrodes of a singular polarity arranged regularly or irregularly on the elongate shaft 210, along a length of the elongate shaft 210 and/or the distal portion 214 of the elongate shaft 210, and/or around a circumference of the elongate shaft 210. In some embodiments, the stenosis and/or the at least partial occlusion 16 may include non-concentric tissue ingrowth within the implanted metallic stent 20 and/or the lumen 14 of the body lumen 10. In some embodiments, the at least one electrode 212, when positioned within the implanted metallic stent 20, may be configured to provide directional ablation of the stenosis and/or the at least partial occlusion 16, as seen in FIG. 3B, which may be useful in treating an eccentric stenosis and/or at least partial occlusion 16, or in other situations where directed energy may be desirable. In some embodiments, the at least one electrode 212 may be configured to direct ablation energy toward the non-concentric tissue ingrowth.

Activation of the energy source 40 may cause the first pole (e.g., the implanted metallic stent 20) of the first polarity and the second pole (e.g., the at least one electrode 212) of the second polarity opposition the first polarity of the bipolar ablation device 200 to ablate the stenosis and/or the at least partial occlusion 16 disposed within the lumen of the implanted metallic stent 20. By locating the second pole within the implanted metallic stent 20 forming the first pole, ablation energy is directed and/or focused between the two poles, as shown by the arrows in FIGS. 2, 3A, and 3B. As such, ablation and/or tissue damage outside of the implanted metallic stent 20 may be limited and/or avoided, thereby maintaining the integrity of the body lumen wall 12 while having the ability to treat and/or remove the stenosis and/or the at least partial occlusion 16 disposed within the lumen of the implanted metallic stent 20. Energizing the bipolar ablation device 200 with the at least one electrode 212 disposed within the lumen of the implanted metallic stent 20 may direct ablation energy within the lumen of the implanted metallic stent 20. Some suitable, but non-limiting, examples of materials for the bipolar ablation device 200, the elongate shaft 210, the at least one electrode 212, and/or the electrode lead 220 are discussed below.

As mentioned above, the electrode lead 220 may include an engagement feature 230, such as an electrical contact, connector, terminal or link, configured to releasably contact and/or connect the electrode lead 220 to the implanted metallic stent 20. The engagement feature 230 illustrated in FIG. 2 may include a grasping metallic clip, such as an alligator clip, a spring-loaded pinching structure, and the like. The electrode lead 220 may be positioned adjacent a proximal end of the implanted metallic stent 20 using the endoscope 30. When the electrode lead 220 and/or the engagement feature 230 is advanced out of the endoscope 30, the grasping metallic clip may be actuated to grasp the proximal end of the implanted metallic stent 20, thereby establishing electrical communication therebetween. Some suitable, but non-limiting, examples of materials for the engagement feature 230 and/or the grasping metallic clip are discussed below.

Figure 4:
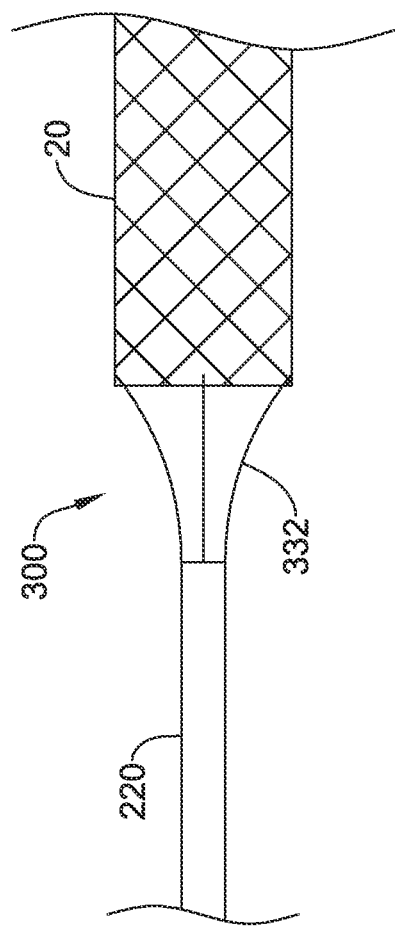
FIGS. 4-7 illustrate example engagement features associated with the bipolar ablation device.

FIGS. 4-7 illustrate alternative and/or example engagement features associated with the electrode lead 220. In one example, FIG. 4 illustrates an engagement feature 330, such as an electrical contact, connector, terminal or link, including at least one flared metallic element 332. In some embodiments, the at least one flared metallic element 332 may include one flared metallic element, two flared metallic elements, three flared metallic elements, four flared metallic elements, five flared metallic elements, six flared metallic elements, seven flared metallic elements, eight flared metallic elements, or more flared metallic elements as desired. The electrode lead 220 may be positioned adjacent a proximal end of the implanted metallic stent 20 with the engagement feature 330 in a collapsed, delivery configuration using the endoscope 30. When the electrode lead 220 and/or the engagement feature 330 is advanced out of the endoscope 30, the at least one flared metallic element 332 may expand and/or deflect radially outward toward an expanded and/or flared configuration and into contact with the implanted metallic stent 20, thereby establishing electrical communication therebetween. In some examples, the engagement feature 330 and/or the at least one flared metallic element 332 may be at least partially disposed within the lumen of the implanted metallic stent 20 and/or may expand and/or deflect into contact with an interior surface of the implanted metallic stent 20. In at least some embodiments, the at least one flared metallic element 332 may be self-biased to be in the expanded and/or flared configuration. Some suitable, but non-limiting, examples of materials for the engagement feature 330 and/or the at least one flared metallic element 332 are discussed below.

Figure 5A:
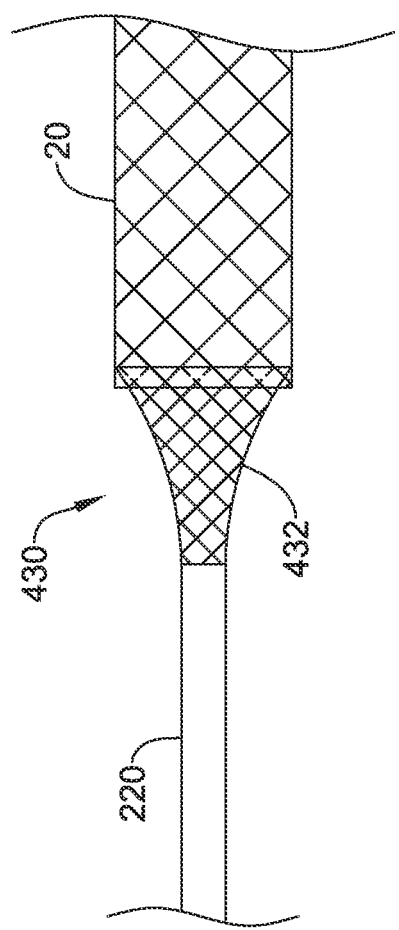
Figure 5B:
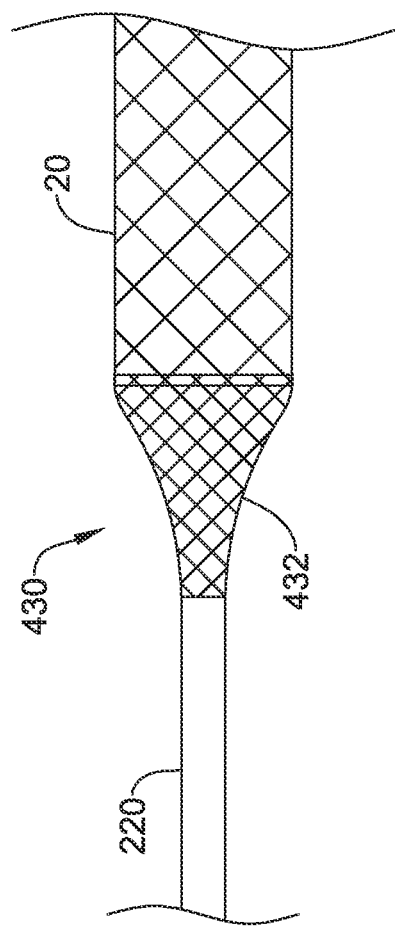

In another example, FIGS. 5A and 5B illustrate an engagement feature 430, such as an electrical contact, connector, terminal or link, including an expandable metallic cage 432. In some embodiments, the expandable metallic cage 432 may be formed as and/or from a stent or other similar structure. The electrode lead 220 may be positioned adjacent the proximal end of the implanted metallic stent 20 in a collapsed, delivery configuration using the endoscope 30. When the electrode lead 220 and/or the engagement feature 430 is advanced out of the endoscope 30, the expandable metallic cage 432 may expand and/or deflect radially outward toward an expanded and/or flared configuration and into contact with the implanted metallic stent 20, thereby establishing electrical communication therebetween. In at least some embodiments, the expandable metallic cage 432 may be self-biased to be in the expanded and/or flared configuration. In some examples, the engagement feature 430 and/or the expandable metallic cage 432 may be at least partially disposed within the lumen of the implanted metallic stent 20 and/or may expand and/or deflect into contact with the interior surface of the implanted metallic stent 20, as seen in FIG. 5A for example. In some examples, the engagement feature 430 and/or the expandable metallic cage 432 may be at least partially disposed around the proximal end of the implanted metallic stent 20 and/or may be advanced over a portion of the proximal end and/or an exterior surface of the implanted metallic stent 20 after expanding and/or deflecting into the expanded and/or flared configuration, as seen in FIG. 5B for example. Some suitable, but non-limiting, examples of materials for the engagement feature 430 and/or the expandable metallic cage 432 are discussed below.

Figure 6:
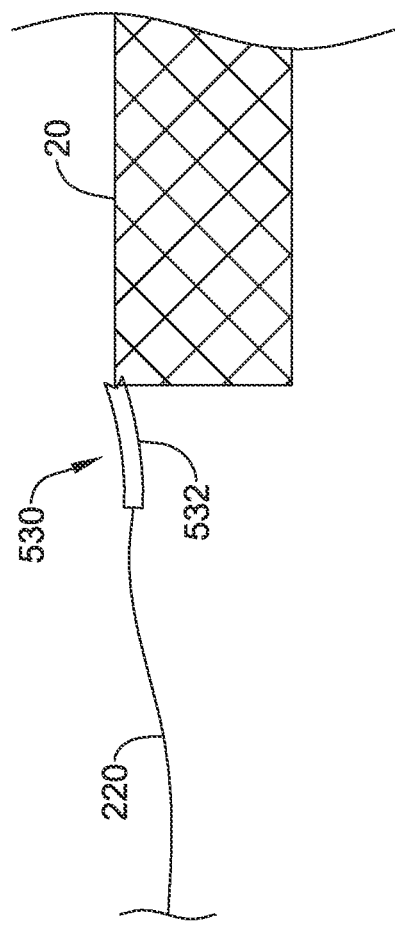

The engagement feature 530, such as an electrical contact, connector, terminal or link, illustrated in FIG. 6 may include a magnetic coupler 532 configured to magnetically engage the implanted metallic stent 20. The electrode lead 220 may be positioned adjacent the proximal end of the implanted metallic stent 20 using the endoscope 30. When the electrode lead 220 and/or the engagement feature 530 is advanced out of the endoscope 30, the magnetic coupler 532 may be manipulated into contact and/or magnetic engagement with the proximal end of the implanted metallic stent 20, thereby establishing electrical communication therebetween. In some examples, the engagement feature 530 and/or the magnetic coupler 532 may be at least partially disposed within the lumen of the implanted metallic stent 20 and/or may expand and/or deflect into contact with the interior surface of the implanted metallic stent 20. Some suitable, but non-limiting, examples of materials for the engagement feature 530 and/or the magnetic coupler 532 are discussed below.

Figure 7:
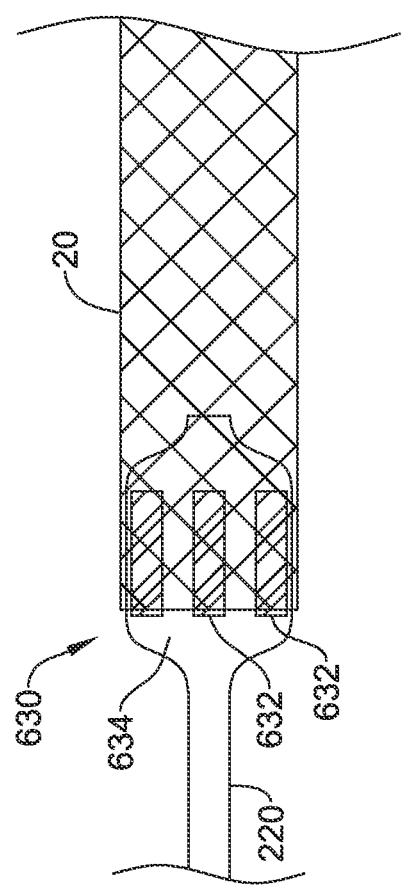

The engagement feature 630, such as an electrical contact, connector, terminal or link, illustrated in FIG. 7 may include at least one electrode element 632 disposed on an outer surface of an inflatable balloon 634. In some embodiments, the at least one electrode element 632 may include one electrode element, two electrode elements, three electrode elements, four electrode elements, five electrode elements, six electrode elements, seven electrode elements, eight electrode elements, or more electrode elements arranged regularly or irregularly on the outer surface of the inflatable balloon 634, along a length of the inflatable balloon 634, and/or around a circumference of the inflatable balloon 634. The electrode lead 220 may be positioned adjacent a proximal end of the implanted metallic stent 20 with the engagement feature 630 in a collapsed, delivery configuration using the endoscope 30. When the electrode lead 220 and/or the engagement feature 630 is advanced out of the endoscope 30, the inflatable balloon 634 may be inflated to expand radially outward toward an expanded and/or flared configuration and urge the at least one electrode element 632 into contact with the implanted metallic stent 20, thereby establishing electrical communication therebetween. In some examples, the engagement feature 630, the inflatable balloon 634, and/or the at least one electrode element 632 may be at least partially disposed within the lumen of the implanted metallic stent 20 and/or may expand into contact with an interior surface of the implanted metallic stent 20. Some suitable, but non-limiting, examples of materials for the engagement feature 630, the at least one electrode element 632, and/or the inflatable balloon 634 are discussed below.

Figure 8A:
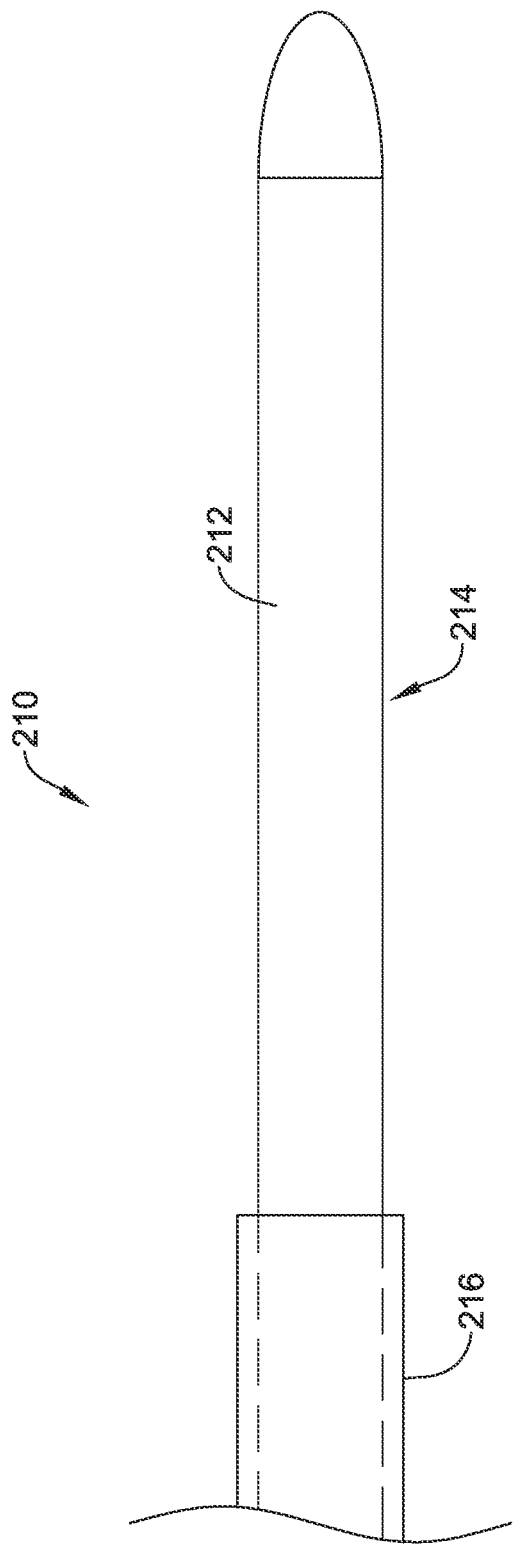
FIG. 8A illustrates an example elongate shaft of a bipolar ablation device.

FIG. 8A illustrates an example configuration of the elongate shaft 210 and/or the at least one electrode 212, such as an elongate probe. In the example shown in FIG. 8A, the at least one electrode 212 is formed from a distal portion 214 and/or a bare portion of the elongate shaft 210 itself. In some embodiments, the elongate shaft 210 may be a solid shaft or rod of metallic material. In some embodiments, the elongate shaft 210 may be a hollow tube or tubular member of metallic material. Alternatively, in some embodiments, the elongate shaft 210 may be formed from a non-metallic, electrically-conductive material. As seen in FIG. 8A, in some embodiments, the elongate shaft 210 may include an insulator 216 diposed over and/or on at least a portion of the elongate shaft 210 proximal of the at least one electrode 212. An elongate shaft 210 having at least one electrode 212 configured as shown in FIG. 8A may be suitable for omnidirectional ablation of the stenosis and/or the at least partial occlusion 16 when the elongate shaft 210 is disposed within the lumen of the implanted metallic stent 20. Additionally and/or alternatively, extending the insulator 216 over a portion of the distal portion 214 of the elongate shaft 210 may create and/or result in the at least one electrode 212 being suitable for directional ablation of the stenosis and/or the at least partial occlusion 16 when the elongate shaft 210 is disposed within the lumen of the implanted metallic stent 20. For example, by covering one side of the distal portion 214 of the elongate shaft 210 with the insulator 216, the at least one electrode 212 may directionally ablate the stenosis and/or the at least partial occlusion 16 toward and/or adjacent an opposing side of the distal portion 214 of the elongate shaft 210 when the elongate shaft 210 is disposed within the lumen of the implanted metallic stent 20.

Figure 8B:
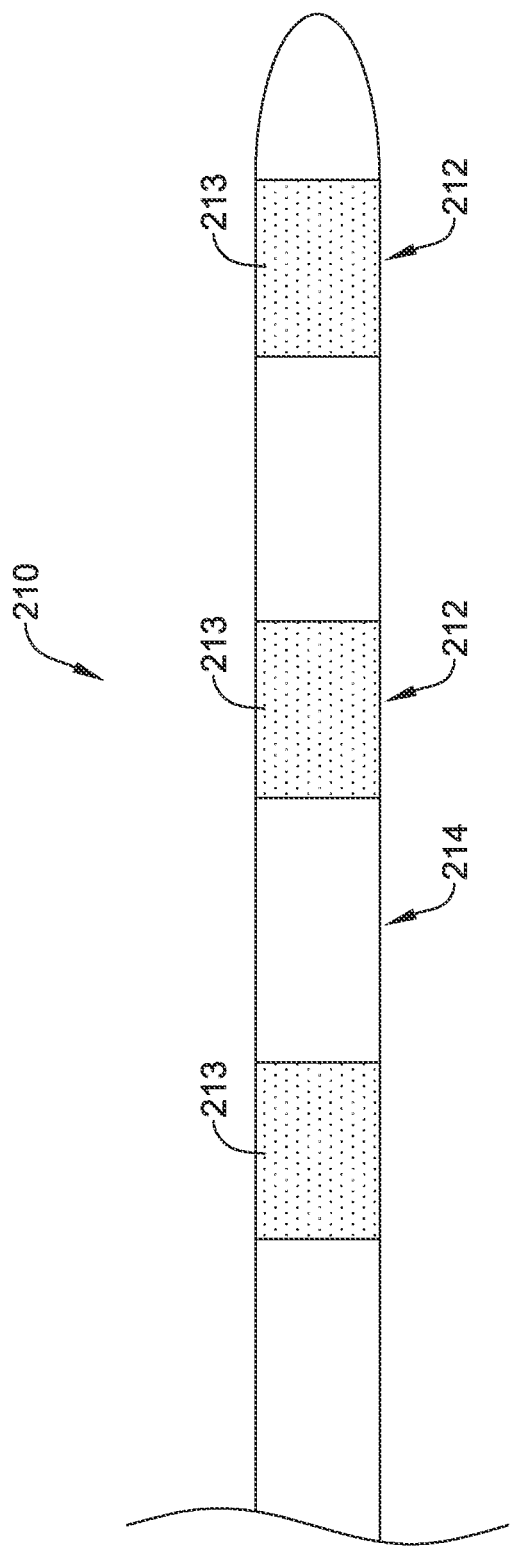
FIG. 8B illustrates another example elongate shaft of a bipolar ablation device.

FIG. 8B illustrates another example configuration of the elongate shaft 210 and/or the at least one electrode 212. In the example shown in FIG. 8B, the at least one electrode 212 comprises a plurality of discrete electrodes 213 disposed along the length of the elongate shaft 210 and/or along the distal portion 214 of the elongate shaft 210. In some embodiments, the plurality of discrete electrodes 213 may be axially and/or longitudinally spaced apart from each other along the length of the elongate shaft 210 and/or along the distal portion 214 of the elongate shaft 210. In some embodiments, the plurality of discrete electrodes 213 may be configured for omnidirectional ablation of the stenosis and/or the at least partial occlusion 16 when the elongate shaft 210 is disposed within the lumen of the implanted metallic stent 20. In some embodiments, the plurality of discrete electrodes 213 may be configured for directional ablation of the stenosis and/or the at least partial occlusion 16 when the elongate shaft 210 is disposed within the lumen of the implanted metallic stent 20. In some embodiments, the directional ablation may be toward a single side of the elongate shaft 210. In some embodiments, the directional ablation may alternate and/or change directions at each successive electrode along the length of the elongate shaft 210 and/or along the distal portion 214 of the elongate shaft 210.

Figure 8C:
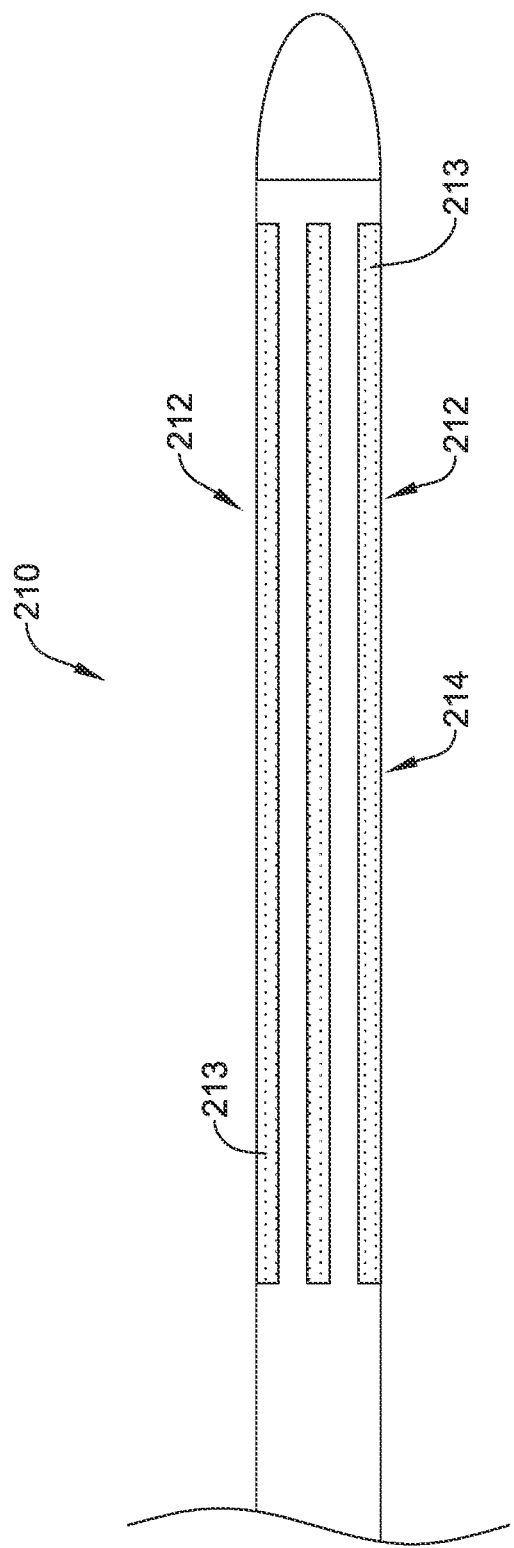
FIG. 8C illustrates another example elongate shaft of a bipolar ablation device.

FIG. 8C illustrates another example configuration of the elongate shaft 210 and/or the at least one electrode 212. In the example shown in FIG. 8C, the at least one electrode 212 comprises a plurality of discrete electrodes 213 disposed circumferentially around the circumference of the elongate shaft 210 and/or disposed circumferentially around the circumference of the distal portion 214 of the elongate shaft 210. In some embodiments, the plurality of discrete electrodes 213 may be circumferentially spaced apart from each other around the circumference of the elongate shaft 210 and/or around the circumference of the distal portion 214 of the elongate shaft 210. In some embodiments, the plurality of discrete electrodes 213 may be configured for omnidirectional ablation of the stenosis and/or the at least partial occlusion 16 when the elongate shaft 210 is disposed within the lumen of the implanted metallic stent 20. In some embodiments, the plurality of discrete electrodes 213 may be configured for directional ablation of the stenosis and/or the at least partial occlusion 16 when the elongate shaft 210 is disposed within the lumen of the implanted metallic stent 20. In some embodiments, the directional ablation may be toward a single side of the elongate shaft 210. In some embodiments, the directional ablation may alternate and/or change directions at each successive electrode around the circumference of the elongate shaft 210 and/or around the circumference of the distal portion 214 of the elongate shaft 210.

Figure 8D:
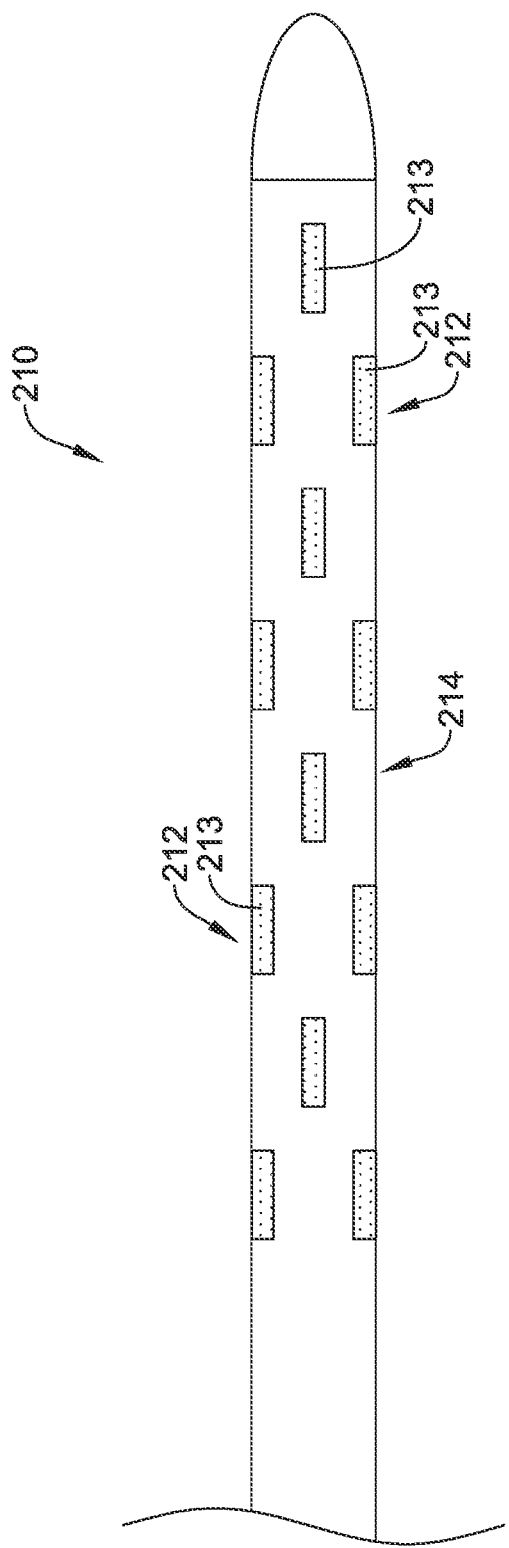
FIG. 8D illustrates another example elongate shaft of a bipolar ablation device.

Combinations and variations of omnidirectional and/or directional ablation along the length and/or circumference of the elongate shaft 210, such as along the length and/or circumference of the distal portion 214 of the elongate shaft 210 are also contemplated, such as shown in FIG. 8D.

Figure 9:
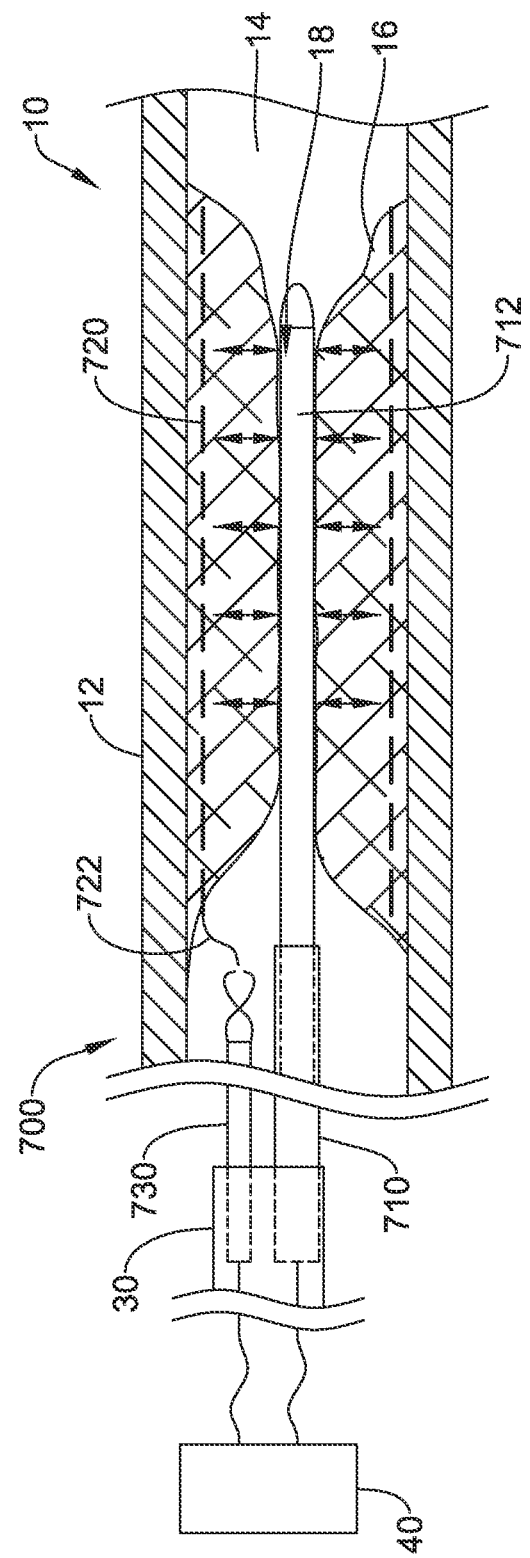
FIG. 9 is a schematic partial cross-sectional view illustrating an example bipolar ablation device and/or system.

FIG. 9 illustrates a system 700 for maintaining patency of a lumen 14 of a body lumen 10. The system may comprise a metallic stent 720 configured for implantation in the the lumen 14 of the body lumen 10, and an elongate shaft 710 slidably disposable within an endoscope 30 and configured to extend into a lumen of the metallic stent 720. The elongate shaft 710 may include at least one electrode 712 configured to form a first pole of a bipolar ablation device, such as and/or including any of those described herein. In one example, the metallic stent 720 may be designed particularly for use with the bipolar ablation device. In some embodiments, the metallic stent 720 may include an electrode lead, contact or terminal 722 electrically engageable with a probe 730 extendable through the endoscope 30, wherein the probe 730 is in electrical communication with an energy source. The electrode lead 722 may be electrically engageable with the probe 730 extendable through the endoscope 30 such that the metallic stent 720 forms a second pole of the bipolar ablation device when the probe 730 is electrically engaged with the metallic stent 720 and an energy source is activated while in electrical communication with the at least one electrode 712 and the probe 730 and/or the electrode lead 722.

In some uses or applications, it may be expected and/or anticipated by the practitioner that the body lumen 10 will undergo and/or develop tissue ingrowth forming an at least partial occlusion 16 (e.g., stenosis, etc.) of the lumen 14 of the body lumen 10 following implantation of the metallic stent 720. By designing the metallic stent 720 with the electrode lead, contact or terminal 722 incorporated therein, it may be easier and/or more efficient to electrically engage the metallic stent 720 with the probe 730 during a later and/or subsequent procedure to ablation the at least partial occlusion 16 (e.g., stenosis, etc.) of the lumen 14 of the body lumen 10 and thereby re-open the lumen 14 of the body lumen 10 and maintain the patency thereof over time. The probe 730 may be formed as in any of the engagement features disclosed herein, as well as others. In at least some embodiments, energization of the bipolar ablation device may direct ablation energy within the lumen of the metallic stent 720. In some embodiments, ablation may be substantially limited to the at least partial occlusion 16 (e.g., stenosis, etc.) of the lumen 14 of the body lumen 10 disposed within the lumen of metallic stent 720. In some embodiments, ablation and/or tissue damage outside of the metallic stent 720 may be limited and/or avoided, thereby maintaining the integrity of the body lumen 10 while having the ability to treat and/or remove the stenosis and/or the at least partial occlusion 16 disposed within the lumen of the metallic stent 720. Some suitable, but non-limiting, examples of materials for the elongate shaft 710, the at least one electrode 712, the metallic stent 720, the electrode lead 722, and/or the probe 730 are discussed below.

Figure 10:
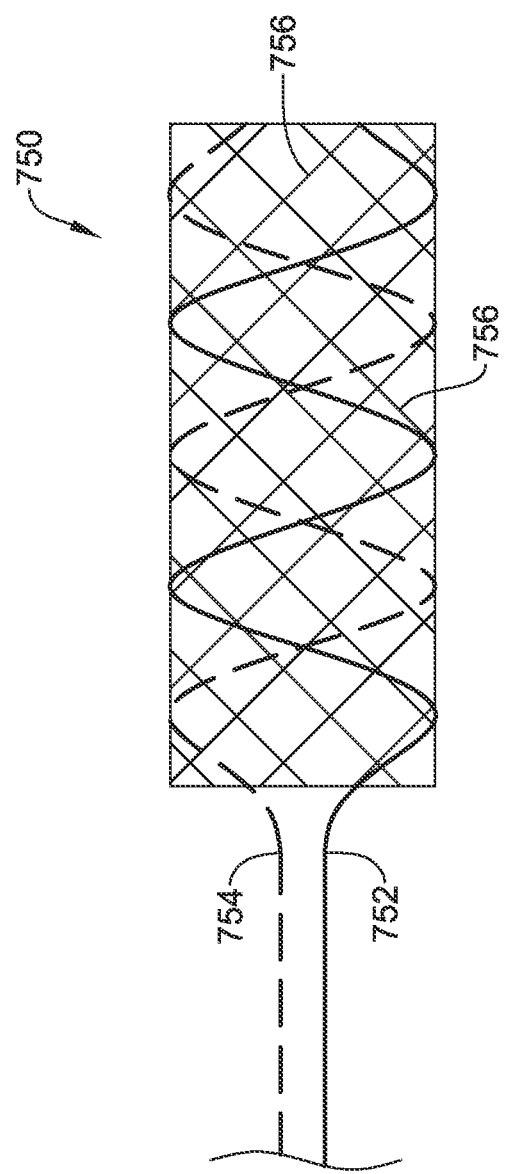
FIG. 10 illustrates an example metallic stent of a bipolar ablation device.

In some embodiments, a system for maintaining patency of the lumen 14 of the body lumen 10 may include a metallic stent 750 and/or an energy source electrically connectable thereto to form a bipolar ablation device. The metallic stent 750 may comprise a first electrode wire 752 configured to form a first pole of the bipolar ablation device, a second electrode wire 754 spaced apart from the first electrode wire 752, the second electrode wire 754 being configured to to form a second pole of the bipolar ablation device, and at least one non-conductive filament 756 interwoven with the first electrode wire 752 and the second electrode wire 754, as seen in FIG. 10 for example. In some embodiments, the metallic stent 750 may be a braided stent, a knitted stent, a woven stent, or similar structure. For the purpose of this disclosure, the term "interwoven" may generally be understood to encompass a configuration involving an alternating over and under relationship between the first electrode wire 752, the second electrode wire 754, and/or the at least one non-conductive filament 756.

In some embodiments, the metallic stent 750 may form a substantially tubular and/or cylindrical structure in a relaxed configuration, an unstressed configuration, and/or an unconstrained configuration. In some embodiments, the first electrode wire 752 may extend helically around a central longitudinal axis of the metallic stent 750 in a first direction. The second electrode wire 754 may extend helically around the central longitudinal axis of the metallic stent 750 in the first direction spaced apart from and parallel to the first electrode wire 752. The first electrode wire 752 and the second electrode wire 754 may be spaced apart from each other axially. For example, in at least some embodiments, the first electrode wire 752 and the second electrode wire 754 do not engage and/or contact each other. The first electrode wire 752 and the second electrode wire 754 may form the first pole and the second pole, respectively, of the bipolar ablation device such that when energized, ablation energy extends between the first pole and the second pole. In some embodiments, the ablation energy may extend both inside and outside of the metallic stent 750.

In some embodiments, the at least one non-conductive filament 756 of the metallic stent 750 may include one non-conductive filament, two non-conductive filaments, three non-conductive filaments, four non-conductive filaments, five non-conductive filaments, six non-conductive filaments, seven non-conductive filaments, eight non-conductive filaments, nine non-conductive filaments, ten non-conductive filaments, or another suitable number of non-conductive filaments. In some embodiments, the at least one non-conductive filament 756 (for example, at least one of the at least one non-conductive filament, but not necessarily each or all of the at least one non-conductive filament), may extend helically around the central longitudinal axis of the metallic stent 750 in a second direction opposite the first direction. In some embodiments, the at least one non-conductive filament 756 may extend in both the first direction and the second direction (for example, one or more filaments may extend in the first direction and one or more filaments may extend in the second direction).

The first electrode wire 752 and the second electrode wire 754 may be electrically connectable to an energy source configured to supply bipolar ablation energy. The at least one non-conductive filament 756 may be non-conductive, such that ablation energy is limited to space(s) between the first electrode wire 752 and the second electrode wire 754. In some embodiments, the at least one non-conductive filament 756 may be non-metallic, such as a polymeric material. In some embodiments, the at least one non-conductive filament 756 may be formed from a metallic material covered and/or coated with an insulator and/or a non-conductive material. Some suitable, but non-limiting, examples of materials for the metallic stent 750, the first electrode wire 752, the second electrode wire 754, and/or the at least one non-conductive filament 756 are discussed below.

Figure 11:
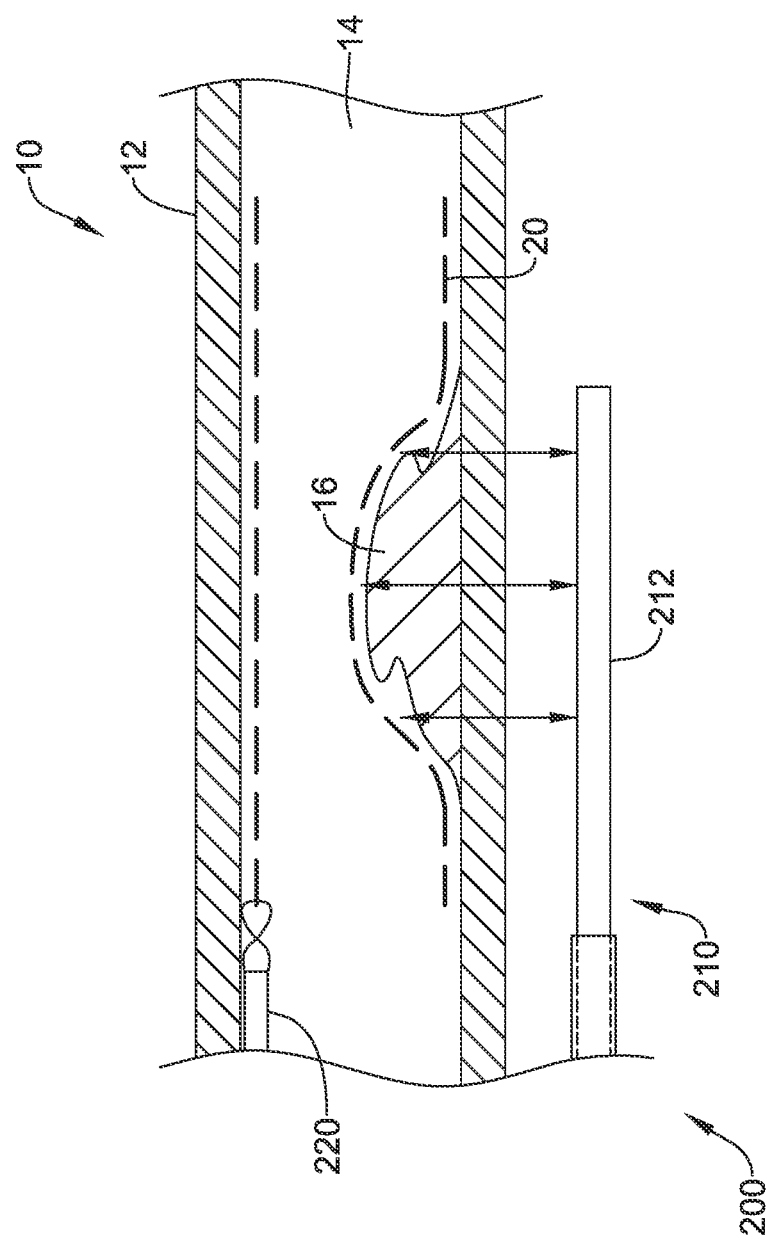
FIG. 11 is a schematic partial cross-sectional view illustrating aspects of an alternative bipolar ablation device.

FIG. 11 illustrates an alternative use of the bipolar ablation device 200. In this arrangement, the elongate shaft 210 and the at least one electrode 212 may be positioned outside of the lumen 14 of the body lumen 10. The metallic stent 20 may be positioned within the lumen 14 of the body lumen 10 in apposition with the body lumen wall 12 and/or the stenosis and/or the at least partial occlusion 16 disposed therein. The alternative use illustrated in FIG. 11 may be useful for treating cancerous tumors, growths, or other undesirable features of the body lumen wall 12. Positioning the elongate shaft 210 and/or the at least one electrode 212 (e.g., the first pole of the bipolar ablation device) outside of the metallic stent 20 (e.g., the second pole of the bipolar ablation device) may create a controlled ablation zone outside of the metallic stent 20 between the metallic stent 20 and the elongate shaft 210 and/or the at least one electrode 212.

Figure 12:
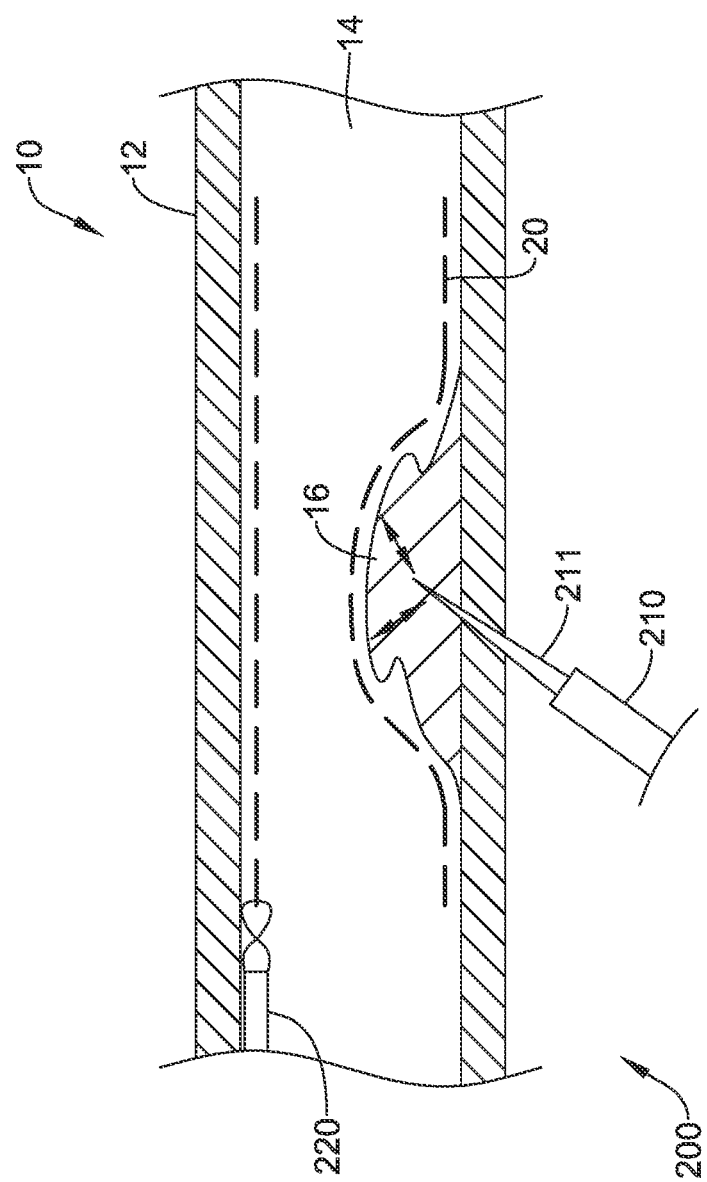
FIG. 12 is a schematic partial cross-sectional view illustrating aspects of an alternative bipolar ablation device.

FIG. 12 illustrates another alternative use of the bipolar ablation device 200. In this arrangement, the at least one electrode 212 may include and/or comprise a needle electrode 211 at a distal end of the elongate shaft 210. Similar to the embodiment of FIG. 11 above, the elongate shaft 210 and/or the at least one electrode 212 (e.g., the needle electrode 211) may be positioned outside of the lumen of the metallic stent 20. The metallic stent 20 may be positioned within the lumen 14 of the body lumen 10 in apposition with the body lumen wall 12 and/or the stenosis and/or the at least partial occlusion 16 disposed therein. The alternative use illustrated in FIG. 12 may be useful for directly treating cancerous tumors, growths, or other undesirable features of the body lumen wall 12, while limiting or avoiding ablation and/or damage outside of the body lumen wall 12. The at least one electrode 212 (e.g., the needle electrode 211) may be inserted directly into the stenosis and/or the at least partial occlusion 16. Positioning the elongate shaft 210 and/or the at least one electrode 212 (e.g., the first pole of the bipolar ablation device) outside of the metallic stent 20 (e.g., the second pole of the bipolar ablation device) may create a controlled ablation zone outside of the metallic stent 20 between the metallic stent 20 and the at least one electrode 212 (e.g., the needle electrode 211).

Figure 13:
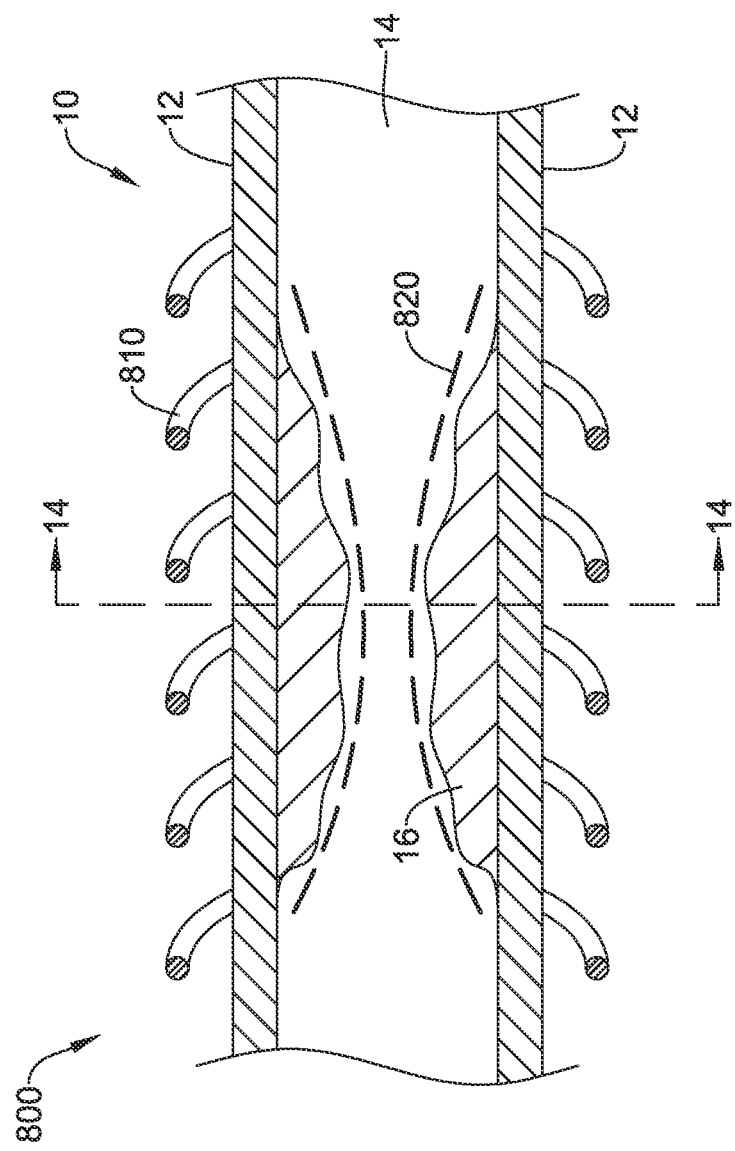
FIG. 13 is a schematic partial cross-sectional view illustrating aspects of an ablation device utilizing induction heating.
Figure 13A:
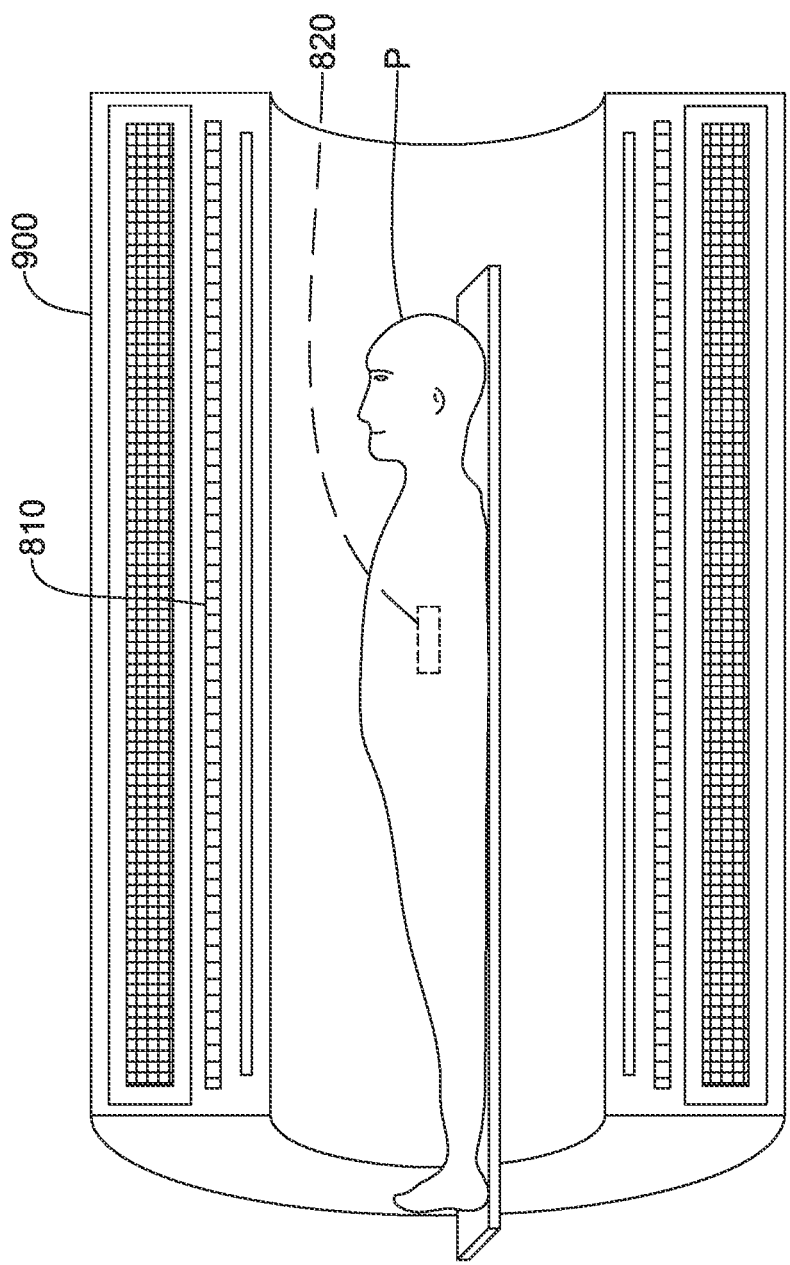
FIG. 13A is a schematic partial cross-sectional view illustrating aspects of an ablation device utilizing induction heating.
Figure 14:
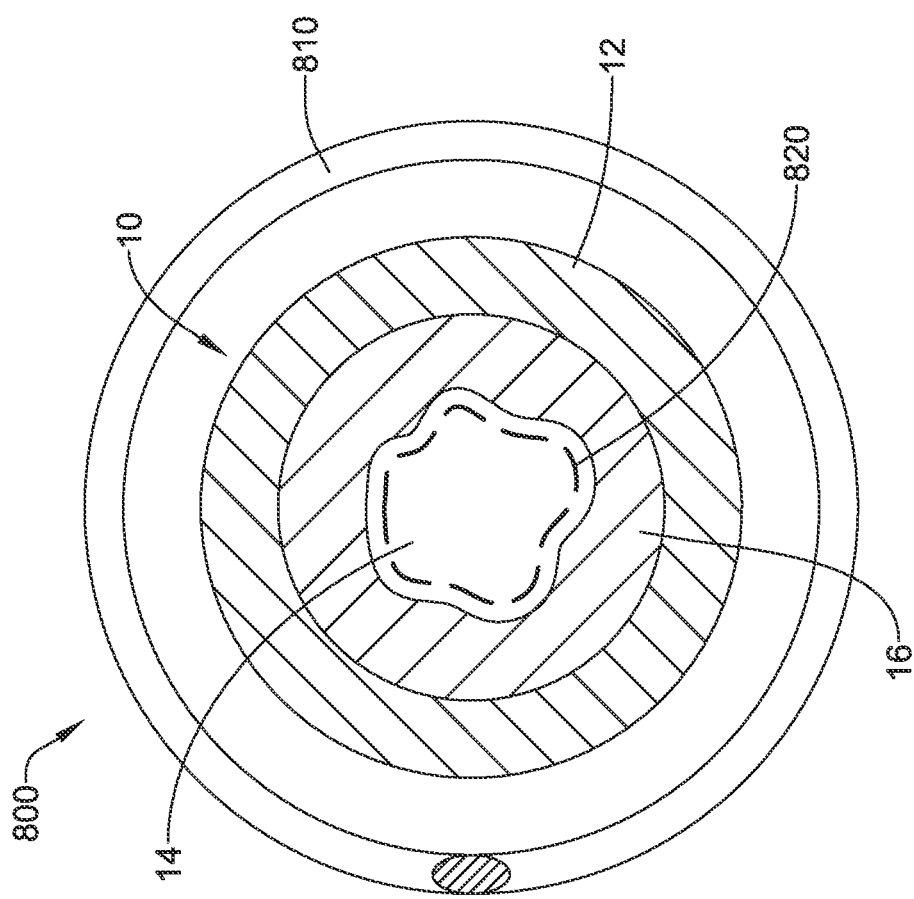
FIG. 14 is a cross-sectional view taken along the line 14-14 of FIG. 13.

FIG. 13 illustrates a system 800 for treating the stenosis and/or the at least partial occlusion 16 disposed within the lumen 14 of the body lumen 10. Similar to other embodiments described herein, the system 800 may include a metallic stent 820 disposed within the lumen 14 of the body lumen 10 in apposition with the body lumen wall 12 and/or the stenosis and/or the at least partial occlusion 16. The metallic stent 820 may be a previously-implanted metallic stent or the metallic stent 820 may be implanted during a procedure using the system 800. The system 800 may include an induction coil 810 coupleable to an AC energy source. Alternating current in the induction coil 810 may produce oscillating magnetic fields that induce alternating current within the metallic stent 820. Since the alternating current has nowhere to go (e.g., no outlet), the current causes heating of the metallic stent 820. In use, the system 800 may externally heat the metallic stent 820 using AC induction, thereby providing hyperthermic treatment to the affected areas around the metallic stent 820 (e.g., the stenosis and/or the at least partial occlusion 16). In some embodiments, the metallic stent 820 may instead be a non-metallic stent having ferric particles embedded therein. One benefit of the system 800, particularly when utilizing a previously-implanted metallic stent, is that a percutaneous and/or surgical procedure is unnecessary to conduct ablation/treatment. Instead, the induction coil 810 may be disposed around the metallic stent 820 (and/or the previously-implanted metallic stent), and/or may be external to the patient (e.g., FIG. 13A) and/or the body lumen 10 (e.g., FIG. 14). For example, the patient P may be disposed within an MRI machine 900 or other device including an induction coil 810. In some embodiments, a single body part (e.g., an arm, a leg, etc.) of the patient P having the metallic stent 820 implanted therein may be disposed within the MRI machine 900 or other device including the induction coil 810. The system 800 may be useful when treating a cancerous duct, for example. The metallic stent 820 may be disposed (either previously or during a concurrent procedure) within the cancerous duct and/or the lumen 14 of the body lumen 10, which may push and/or urge the stenosis and/or the at least partial occlusion 16 radially outward and/or toward the body lumen wall 12. When energized, the system 800 may ablate and/or treat tissue (e.g., the stenosis and/or the at least partial occlusion 16) disposed inside and/or outside of the metallic stent 820. However, the tissue is not heated directly by the ablation energy, as in RF ablation for example, but is indirectly (e.g., radiantly) heated by the metallic stent 820. Some suitable, but non-limiting, examples of materials for the induction coil 810 and/or the metallic stent 820 are discussed below.

Figure 15:
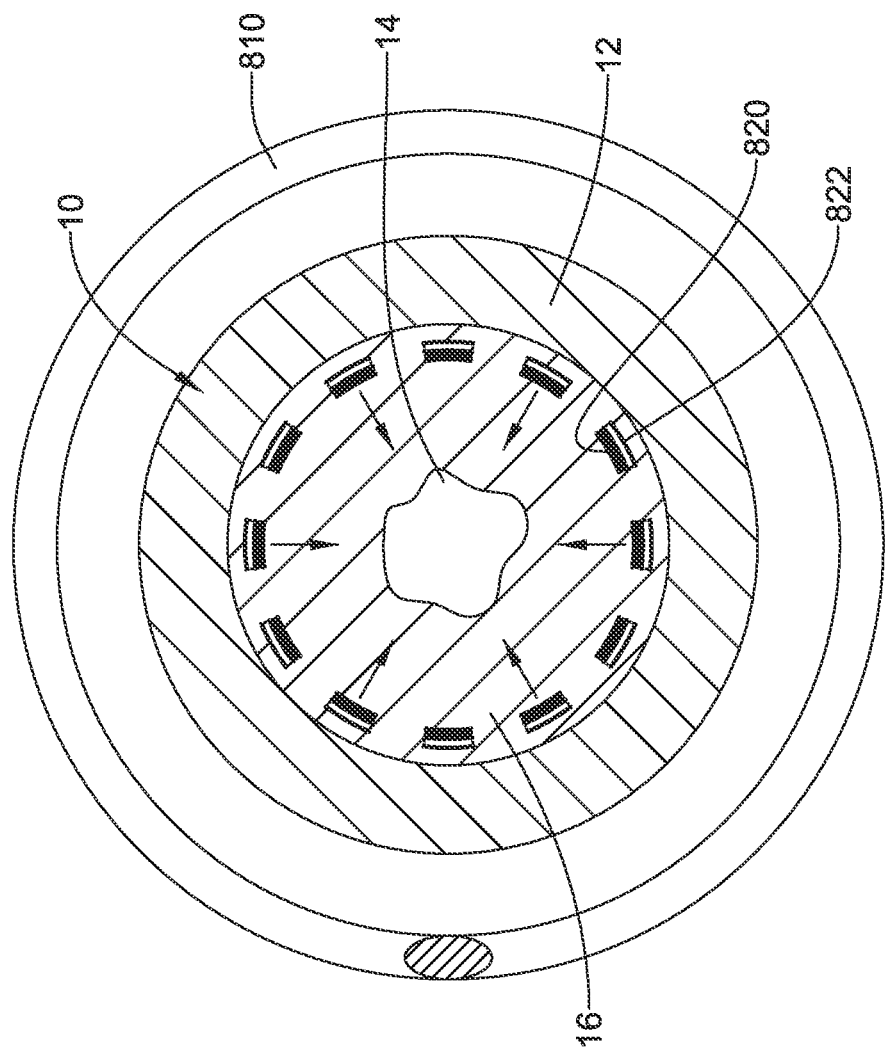
FIG. 15 illustrates an alternative configuration of a metallic stent associated with disclosure.

In some embodiments, the metallic stent 820 may include an insulation layer 822 disposed on and/or around an outer surface of the metallic stent 820 (i.e., the radially outward surface of the metallic stent 820), while an inner surface of the metallic stent 820 (i.e., the radially inward surface of the metallic stent 820) is devoid of the insulation layer 822 leaving a metallic surface of the metallic stent 820 exposed, as seen in FIG. 15. In some embodiments, the insulation layer 822 may be non-metallic, a polymeric material, a ceramic material, a composite material, and/or combinations thereof. The insulation layer 822 may protect adjacent tissue, such as the body lumen wall 12 for example, from heating and/or ablation. The insulation layer 822 may be particularly useful when the metallic stent 820 is implanted and left in place over time, during which the metallic stent 820 and/or the lumen 14 of the body lumen 10 may become at least partially occluded by the stenosis and/or the at least partial occlusion 16. In such a situation, the metallic stent 820 with the insulation layer 822 formed thereon may act as a "self-cleaning" stent. When the metallic stent 820 is heated, using induction heating for example, the heat and/or energy is directed inwardly within the lumen of the metallic stent 820 and/or the lumen 14 of the body lumen 10, thereby ablating the stenosis and/or the at least partial occlusion 16 disposed within the lumen of the metallic stent 820. Other configurations and/or means of heating the metallic stent 820 are also contemplated. Some suitable, but non-limiting, examples of materials for the insulation layer 822 are discussed below.

The materials that can be used for the various components of the system, the elongate shaft, the at least one electrode, the metallic stent, the endoscope, the electrode lead, the engagement feature(s), the first and second electrode wires, the at least one non-conductive filament, etc. (and/or other systems or components disclosed herein) and the various elements thereof disclosed herein may include those commonly associated with medical devices. For simplicity purposes, the following discussion makes reference to the system, the elongate shaft, the at least one electrode, the metallic stent, the endoscope, the electrode lead, the engagement feature(s), the first and second electrode wires, the at least one non-conductive filament, etc. However, this is not intended to limit the devices and methods described herein, as the discussion may be applied to other elements, members, components, or devices disclosed herein.

In some embodiments, the system, the elongate shaft, the at least one electrode, the metallic stent, the endoscope, the electrode lead, the engagement feature(s), the first and second electrode wires, the at least one non-conductive filament, etc., and/or components thereof may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; platinum; palladium; gold; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the system, the elongate shaft, the at least one electrode, the metallic stent, the endoscope, the electrode lead, the engagement feature(s), the first and second electrode wires, the at least one non-conductive filament, etc., and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the system, the elongate shaft, the at least one electrode, the metallic stent, the endoscope, the electrode lead, the engagement feature(s), the first and second electrode wires, the at least one non-conductive filament, etc. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the system, the elongate shaft, the at least one electrode, the metallic stent, the endoscope, the electrode lead, the engagement feature(s), the first and second electrode wires, the at least one non-conductive filament, etc. to achieve the same result.

In some embodiments, a degree of Magnetic Resonance Imaging (MRI) compatibility is imparted into the system, the elongate shaft, the at least one electrode, the metallic stent, the endoscope, the electrode lead, the engagement feature(s), the first and second electrode wires, the at least one non-conductive filament, etc. For example, the system, the elongate shaft, the at least one electrode, the metallic stent, the endoscope, the electrode lead, the engagement feature(s), the first and second electrode wires, the at least one non-conductive filament, etc., and/or components or portions thereof, may be made of a material that does not substantially distort the image and create substantial artifacts (e.g., gaps in the image). Certain ferromagnetic materials, for example, may not be suitable because they may create artifacts in an MRI image. The system, the elongate shaft, the at least one electrode, the metallic stent, the endoscope, the electrode lead, the engagement feature(s), the first and second electrode wires, the at least one non-conductive filament, etc., or portions thereof, may also be made from a material that the MRI machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the system, the elongate shaft, the at least one electrode, the metallic stent, the endoscope, the electrode lead, the engagement feature(s), the first and second electrode wires, the at least one non-conductive filament, etc., and/or portions thereof, may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments, the sheath can be blended with a liquid crystal polymer (LCP). For example, the mixture can contain up to about 6 percent LCP.

In some embodiments, the elongate shaft, the endoscope, the electrode lead, the engagement feature(s), the at least one non-conductive filament, etc. disclosed herein may include a fabric material disposed over or within at least a portion of the structure. The fabric material may be composed of a biocompatible material, such a polymeric material or biomaterial. In some embodiments, the fabric material may include a bioabsorbable material. Some examples of suitable fabric materials include, but are not limited to, polyethylene glycol (PEG), nylon, polytetrafluoroethylene (PTFE, ePTFE), a polyolefinic material such as a polyethylene, a polypropylene, polyester, polyurethane, and/or blends or combinations thereof.

In some embodiments, the elongate shaft, the endoscope, the electrode lead, the engagement feature(s), the at least one non-conductive filament, etc. may include a textile material. Some examples of suitable textile materials may include synthetic yarns that may be flat, shaped, twisted, textured, pre-shrunk or un-shrunk. Synthetic biocompatible yarns suitable for use in the present invention include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun-types. The type and denier of the yarn chosen may be selected in a manner which forms a biocompatible and implantable prosthesis and, more particularly, a vascular structure having desirable properties.

In some embodiments, the system, the elongate shaft, the at least one electrode, the metallic stent, the endoscope, the electrode lead, the engagement feature(s), the first and second electrode wires, the at least one non-conductive filament, etc. may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A method of treating a stenosis within a previously implanted metallic stent, comprising:
    advancing an endoscope to a position adjacent the previously implanted metallic stent;
    advancing an elongate shaft from the endoscope and into a lumen of the previously implanted metallic stent such that the elongate shaft is spaced apart from the previously implanted metallic stent, wherein an exposed metallic distal portion of the elongate shaft forms at least one electrode configured to form a first pole of a bipolar ablation device;
    separately advancing an electrode lead that is spaced apart from the elongate shaft from the endoscope and into electrical contact with the previously implanted metallic stent such that the previously implanted metallic stent forms a second pole of the bipolar ablation device; and
    ablating the stenosis by energizing the bipolar ablation device with the electrode lead in electrical contact with the previously implanted metallic stent and the at least one electrode disposed within the lumen of the previously implanted metallic stent and spaced apart radially inward from the previously implanted metallic stent.

2. The method of claim 1, wherein the electrode lead includes an engagement feature configured to releasably contact the electrode lead to the previously implanted metallic stent.

3. The method of claim 2, wherein the engagement feature includes a grasping metallic clip.

4. The method of claim 2, wherein the engagement feature includes at least one flared metallic element.

5. The method of claim 2, wherein the engagement feature includes an expandable metallic cage.

6. The method of claim 2, wherein the engagement feature includes a magnetic coupler.

7. The method of claim 2, wherein the engagement feature includes at least one electrode element disposed on an outer surface of an inflatable balloon.

8. The method of claim 1, wherein the elongate shaft includes an insulator disposed over at least a portion of the elongate shaft proximal of the exposed metallic distal portion.

9. The method of claim 1, wherein energizing the bipolar ablation device provides omnidirectional ablation energy between the at least one electrode and the previously implanted metallic stent.

10. The method of claim 9, wherein the at least one electrode extends about an entire circumference of the elongate shaft.

11. The method of claim 1, wherein energizing the bipolar ablation device provides non-omnidirectional ablation energy between the at least one electrode and the previously implanted metallic stent.

12. The method of claim 11, wherein the at least one electrode extends about only a portion of a circumference of the elongate shaft.

13. A method of treating a stenosis within a previously implanted metallic stent, comprising:
    advancing an endoscope to a position adjacent the previously implanted metallic stent;
    advancing an exposed metallic distal portion of an elongate shaft from the endoscope and into a lumen of the previously implanted metallic stent such that the exposed metallic distal portion is spaced apart from the previously implanted metallic stent, wherein the exposed metallic distal portion forms a first pole of a bipolar ablation device, wherein a length of the exposed metallic distal portion is equal to or greater than 25% of a length of the previously implanted metallic stent;
    separately advancing an electrode lead that is spaced apart from the elongate shaft from the endoscope and into electrical contact with the previously implanted metallic stent such that the previously implanted metallic stent forms a second pole of the bipolar ablation device; and
    ablating the stenosis by energizing the bipolar ablation device with the electrode lead in electrical contact with the previously implanted metallic stent and the exposed metallic distal portion disposed within the lumen of the previously implanted metallic stent and spaced apart radially inward from the previously implanted metallic stent.

14. The method of claim 13, wherein the length of the exposed metallic distal portion is equal to or greater than 50% of the length of the previously implanted metallic stent.

15. The method of claim 13, wherein the exposed metallic distal portion extends around only a portion of a circumference of the elongate shaft.

16. The method of claim 15, wherein energizing the bipolar ablation device with the electrode lead in electrical contact with the previously implanted metallic stent and the exposed metallic distal portion disposed within the lumen of the previously implanted metallic stent and spaced apart radially inward from the previously implanted metallic stent provides directional ablation of the stenosis within the previously implanted metallic stent.

17. The method of claim 13, wherein the exposed metallic distal portion extends completely around a circumference of the elongate shaft.

18. The method of claim 17, wherein energizing the bipolar ablation device with the electrode lead in electrical contact with the previously implanted metallic stent and the exposed metallic distal portion disposed within the lumen of the previously implanted metallic stent and spaced apart radially inward from the previously implanted metallic stent provides onmidirectional ablation of the stenosis within the previously implanted metallic stent.

19. The method of claim 13, wherein the electrode lead includes an engagement feature configured to releasably contact the electrode lead to the previously implanted metallic stent.

20. The method of claim 19, wherein advancing the electrode lead that is spaced apart from the elongate shaft from the endoscope and into electrical contact with the previously implanted metallic stent includes releasably engaging the engagement feature with the previously implanted metallic stent.

* * * * *